(12) United States Patent
Ankenbauer et al.

(10) Patent No.: US 7,910,720 B2
(45) Date of Patent: Mar. 22, 2011

(54) POLYANION FOR IMPROVED NUCLEIC ACID AMPLIFICATION

(75) Inventors: Waltraud Ankenbauer, Penzberg (DE); Dieter Heindl, Paehl (DE); Frank Laue, Paehl-Fischen (DE); Eva Walter, Bichl (DE); Renate Kolb, Iffeldorf (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 36 days.

(21) Appl. No.: 12/547,013

(22) Filed: Aug. 25, 2009

(65) Prior Publication Data

US 2010/0255547 A1 Oct. 7, 2010

(30) Foreign Application Priority Data

Sep. 9, 2008 (EP) .................. 08015812

(51) Int. Cl.
*C07H 21/04* (2006.01)
*C12P 19/34* (2006.01)
*C12Q 1/68* (2006.01)
*B01L 3/00* (2006.01)

(52) U.S. Cl. .................. 536/24.33; 536/23.1; 536/24.3; 435/6; 435/91.1; 435/91.2; 422/61

(58) Field of Classification Search .................. 536/23.1, 536/24.3, 24.33; 435/6, 91.1, 91.2; 422/61
See application file for complete search history.

(56) References Cited

U.S. PATENT DOCUMENTS

| | | | |
|---|---|---|---|
| 5,118,801 A | 6/1992 | Lizardi et al. | |
| 5,210,015 A | 5/1993 | Gelfand et al. | |
| 5,338,671 A | 8/1994 | Scalice et al. | |
| 5,338,848 A | 8/1994 | Acker et al. | |
| 5,411,876 A | 5/1995 | Bloch et al. | |
| 5,449,603 A | 9/1995 | Nielson et al. | |
| 5,487,972 A | 1/1996 | Gelfand et al. | |
| 5,677,152 A | 10/1997 | Birch et al. | |
| 5,693,502 A | 12/1997 | Gold et al. | |
| 5,773,258 A | 6/1998 | Birch et al. | |
| 5,792,607 A | 8/1998 | Backman et al. | |
| 5,804,375 A | 9/1998 | Gelfand et al. | |
| 5,985,619 A | 11/1999 | Sutherland et al. | |
| 6,020,130 A | 2/2000 | Gold et al. | |
| 6,174,670 B1 | 1/2001 | Wittwer et al. | |
| 6,241,557 B1 | 6/2001 | Reichardt | |
| 6,403,341 B1 | 6/2002 | Barnes et al. | |
| 6,569,627 B2 | 5/2003 | Wittwer et al. | |
| 6,667,165 B2 | 12/2003 | Peters | |

FOREIGN PATENT DOCUMENTS

EP 0744470 A1 11/1996

(Continued)

OTHER PUBLICATIONS

Chakrabarti, R. et al, "The enhancement of PCR amplification by low molecular weight amides," Nucleic Acids Research 29:11 (2001) 2377-2381.

(Continued)

*Primary Examiner* — Jezia Riley (57) ABSTRACT

The present invention is directed to a novel chemical compound comprising the structure $[X_x\text{-}(CH_2)_m\text{-phosphate-}Y_y]_n$, characterized in that $3 \leq m \leq 6$, $30 \leq n \leq 60$, each x and y is independently from each other 0 or 1, each X and Y is independently from each other any photometrically measurable entity; provided that the terminal X can also be an —OH group or a phosphate group, and further provided that the terminal Y can also be an —OH group. Such a compound can be used as a suitable hot start additive for PCR based amplification of nucleic acids.

9 Claims, 5 Drawing Sheets

FOREIGN PATENT DOCUMENTS

| | | |
|---|---|---|
| EP | 1275735 A1 | 1/2003 |
| EP | 0799888 B1 | 5/2005 |
| GB | 2293238 A | 3/1996 |
| WO | 97/46706 A1 | 12/1997 |
| WO | 97/46707 A1 | 12/1997 |
| WO | 97/46712 A2 | 12/1997 |
| WO | 97/46714 A1 | 12/1997 |
| WO | 99/46400 A1 | 9/1999 |
| WO | 00/68411 A1 | 11/2000 |
| WO | 02/14555 A2 | 2/2002 |
| WO | 2006/119419 A2 | 11/2006 |
| WO | 2007/096182 A1 | 8/2007 |

OTHER PUBLICATIONS

Chou, Q. et al., "Prevention of pre-PCR mis-priming and primer dimerization improves low-copy-number amplifications," Nucleic Acids Research 20:7 (1992) 1717-1723.

Dogan, Z. et al., "5'-Tethered Stillbene Derivatives as Fidelity-and-Affinity-Enhancing Modulators of DNA Duplex Stabiity," J. Am, Chem, Soc. 126 (2004) 4762-4763.

Hengen, P. et al., "Optimizing multiplex and LA-PCR with betaine," TIBS 22 (Jun. 1997) 225-226.

Hildebrand, C. et al., "Action of Heparin on Mammalian Nuclei," Biochimica et Biophysica Acta 447 (1977) 295-311.

Kaboev, O. et al., "Hot Start of the Polymerase Chain Reaction Using DNA Helicases," Bioorg Khim 25 (1999) 398-400.

Kainz, P. et al., "Specificity-Enhanced Hot-Start PCR: Addition of Double-Stranded DNA Fragments Adapted to Annealing Temperature," BioTechniques 28:2 (2000) 278-282.

Kellogg, D. et al., "TaqStart Antibody: "Hot Start" PCR Facilitated by a Neutralizing Monoclonal Antibody Directed Against Taq DNA Polymerase," BioTechniques 16:6 (1994) 1134-1137.

Lin, Y. et al, "Inhibition of Multiple Thermostable DNA Polymerases by a Heterodimeric Aptamer," J. Mol. Biol. 271 (1997) 100-111.

Moretti, T. et al. "Enhancement of PCR Amplification Yield and Specificity Using AmpliTaq Gold DNA Polymerase," BioTechniques 25 (1998) 716-722.

Narayanan, S. et al., "Clamping down on weak terminal base pairs: oligonucleotides with molecular caps as fidelity-enhancing elements at the 5'-3'-terminal residues," Nucleic Acids Research 32:9 (2004) 2901-2911.

Nilsson, J. et al., "Heat-Mediated Activation of Affinity-Immobilized Taq DNA Polymerase," BioTechniques 22:4 (1997) 744-751.

Sharkey, D. et al., "Antibodies as Thermolabile Switches: High Temperature Triggering for the Polymerase Chain Reaction," Bio/Rechnology 12 (May 1994) 506-509.

Sturzenbaum, S. et al., "Transfer RNA Reduces the Formation Primer Artifacts During Quantitative PCR," BioTechniques 27 (Jul. 1999) 50-52.

POLYANION FOR IMPROVED NUCLEIC ACID AMPLIFICATION

RELATED APPLICATIONS

This application claims priority to EP 08015812.4 filed Sep. 9, 2008.

FIELD OF THE INVENTION

The present invention relates to the field of template dependent polymerase catalyzed primer extension reactions such as a polymerase chain reaction (PCR). More precisely, the present invention provides a new method for performing a hot start PCR characterized in that unspecific primer dimer amplification is avoided by means of adding a defined polyanion prior to the amplification reaction.

BACKGROUND OF THE INVENTION

A major problem with nucleic acid amplification and more especially with PCR is the generation of unspecific amplification products. In many cases, this is due to an unspecific oligonucleotide priming and subsequent primer extension event prior to the actual thermocycling procedure itself, since thermostable DNA polymerases are also moderately active at ambient temperature. For example, amplification products due to eventually by chance occurring primer dimerisation and subsequent extension are observed frequently. In order to overcome this problem, it is well known in the art to perform a so called "hot start" PCR, wherein one component essential for the amplification reaction is either separated from the reaction mixture or kept in an inactive state until the temperature of the reaction mixture is being raised for the first time. Since the polymerase cannot function under these conditions, there is no primer elongation during the period when the primers can bind non-specifically. In order to achieve this effect, several methods have been applied:

a) Physical Separation of the DNA Polymerase

The physical separation can be obtained for example by a barrier of solid wax, which separates the compartment containing the DNA polymerase from the compartment containing the bulk of the other reagents. During the first heating step the wax is then melting automatically and the fluid compartments are mixed (Chou, Q., et al., Nucleic Acids Res 20 (1992) 1717-23, U.S. Pat. No. 5,411,876). Alternatively, the DNA polymerase is affinity immobilized on a solid support prior to the amplification reaction and only released into the reaction mixture by a heat mediated release (Nilsson, J., et al., Biotechniques 22 (1997) 744-51). Both methods, however are time consuming and inconvenient to perform.

b) Chemical Modification of DNA Polymerase

For this type of hot start PCR, the DNA polymerase is reversibly inactivated as a result of a chemical modification. More precisely, heat labile blocking groups are introduced into the Taq DNA polymerase which renders the enzyme inactive at room temperature (U.S. Pat. No. 5,773,258). These blocking groups are removed at high temperature during a pre-PCR step such that the enzyme is becoming activated. Such a heat labile modification, for example can be obtained by coupling Citraconic Anhydride or Aconitric Anhydride to the Lysine residues of the enzyme (U.S. Pat. No. 5,677,152). Enzymes carrying such modifications are meanwhile commercially available as Amplitaq Gold (Moretti, T., et al., Biotechniques 25 (1998) 716-22) or FastStart DNA polymerase (Roche Molecular Biochemicals). However, the introduction of blocking groups is a chemical reaction which arbitrarily occurs on all sterically available Lysine residues of the enzyme. Therefore, the reproducibility and quality of chemically modified enzyme preparations may vary and can hardly be controlled.

c) Recombinant Modification of DNA Polymerase

Cold sensitive mutants of Taq polymerase have been prepared by means of genetic engineering. These mutants differ from the wildtype enzyme in that they lack the N-terminus (U.S. Pat. No. 6,241,557). In contrast to native or wild type recombinant Taq polymerase, these mutants are completely inactive below 35° C. and thus may be used in some cases for performing a hot start PCR. However, the N-terminal truncated cold sensitive mutant form requires low salt buffer conditions, has a lower processivity as compared to the wild type enzyme and thus can only be used for the amplification of short target nucleic acids. Moreover, since the truncated form lacks 5'-3' exonuclease activity, it can not be used for real time PCR experiments based on the TaqMan detection format.

d) DNA Polymerase Inhibition by Nucleic Acid Additives

Extension of non-specifically annealed primers has been shown to be inhibited by the addition of short double stranded DNA fragments (Kainz, P., et al., Biotechniques 28 (2000) 278-82). In this case, primer extension is inhibited at temperatures below the melting point of the short double stranded DNA fragment, but independent from the sequence of the competitor DNA itself. However, it is not known, to which extent the excess of competitor DNA influences the yield of the nucleic acid amplification reaction.

Alternatively, oligonucleotide Aptamers with a specific sequence resulting in a defined secondary structure may be used. Such Aptamers have been selected using the SELEX Technology for a very high affinity to the DNA polymerase (U.S. Pat. No. 5,693,502, Lin, Y., and Jayasena, S., D., J. Mol. Biol. 271 (1997) 100-11). The presence of such Aptamers within the amplification mixture prior to the actual thermocycling process itself again results in a high affinity binding to the DNA polymerase and consequently a heat labile inhibition of its activity (U.S. Pat. No. 6,020,130). Due to the selection process, however, all so far available Aptamers can only be used in combination with one particular species of DNA polymerase.

e) Taq DNA Antibodies

An alternative approach to achieve heat labile inhibition of Taq DNA polymerase is the addition of monoclonal antibodies raised against the purified enzyme (Kellogg, D., E., et al., Biotechniques 16 (1994) 1134-7; Sharkey, D., J., et al., Biotechnology (NY) 12 (1994) 506-9). Like the oligonucleotide Aptamers, the antibody binds to Taq DNA polymerase with high affinity at ambient temperatures in an inhibitory manner (U.S. Pat. No. 5,338,671). The complex is resolved in a preheating step prior to the thermocycling process itself. This leads to a substantial time consuming prolongation of the amplification as a whole, especially if protocols for rapid thermocycling are applied (WO 97/46706).

U.S. Pat. No. 5,985,619 discloses a specific embodiment for performing PCR using a hot start antibody, wherein besides Taq polymerase, e.g. Exonuclease III from E. coli is added as a supplement to the amplification mixture in order to digest unspecific primer dimer intermediates. As disclosed above, Exonuclease III recognizes double-stranded DNA as a substrate, like, for example, target/primer-or target/primer extension product hybrids. Digestion is taking place by means of cleavage of the phosphodiester bond at the 5' end of the 3' terminal deoxynucleotide residue. Since this type of exonuclease is active at ambient temperatures, all unspecifically annealed primers and primer extension products therefore are digested. This results in some embodiments in an even enhanced specificity of the amplification reaction. Yet, digestion of the unspecific primers dependent on the duration of the preincubation time may lead to a substantial and uncontrolled decrease in primer concentration, which in turn may affect the amplification reaction itself.

f) Usage of Modified Primers Alone or in Combination with Exonucleases

EP 0 799 888 and GB 2293238 disclose an addition of 3' blocked oligonucleotides to PCR reactions. Due to the 3' block, these oligonucleotides can not act as primers. The blocked oligonucleotides are designed to compete/interact with the PCR primers which results in reduction of nonspecific products.

Another alternative is the use of phosphorothioate oligonucleotide primers in combination with an exonuclease III in the PCR reaction mixes (EP 0 744 470). In this case, a 3' exonuclease, which usually accepts double stranded as well as single stranded DNA substrates, degrades duplex artefacts such as primer dimers as well as carry over amplicons, while leaving the single stranded amplification primers undegraded. Similarly, the usage of primers with a basic modified 3' end and template dependent removal by $E.\ coli$ Endonuclease IV has been suggested (U.S. Pat. No. 5,792,607).

A particular embodiment of the general idea is found in EP 1 275 735. Its specification discloses a composition for performing a nucleic acid amplification reaction comprising (i) a thermostable DNA-polymerase, (ii) a thermostable 3'-5' Exonuclease, and (iii) at least one primer for nucleic acid amplification with a modified 3' terminal residue which is not elongated by said thermostable DNA-polymerase as well as methods for performing a PCR reaction using this composition.

However, it is major drawback of the disclosed alternatives that for each PCR reaction, modified primers are required, which lead to increased requirements regarding increase the cost for each individual assay.

g) Other PCR Additives

Other organic additives known in the art like DMSO, betaines, and formamides (WO 99/46400; Hengen, P. N., Trends Biochem Sci 22 (1997) 225-6; Chakrabarti, R., and Schutt, C. E., Nucleic Acids Res 29 (2001) 2377-81) result in an improvement of amplification of GC rich sequences, rather than prevention of primer dimer formation. Similarly, heparin may stimulate in vitro run-on transcription presumably by removal of proteins like histones in order to make chromosomal DNA accessible (Hildebrand, C. E., et al., Biochimica et Biophysica Acta 477 (1977) 295-311).

It is also known that addition of single strand binding protein (U.S. Pat. No. 5,449,603) or tRNA, (Sturzenbaum, S. R., Biotechniques 27 (1999) 50-2) results in non-covalent association of these additives to the primers. This association is disrupted when heating during PCR. It was also found that addition of DNA helicases prevent random annealing of primers (Kaboev, O. K., et al., Bioorg Khim 25 (1999) 398-400). Furthermore, poly-glutamate (WO 00/68411) in several cases may be used in order to inhibit polymerase activity at low temperatures.

Moreover, it is known that polyanionic polymerase inhibitors may control the activity of thermostable DNA polymerases dependent on the applied incubation temperature. U.S. Pat. No. 6,667,165 discloses a hot start embodiment, characterized in that inactive polymerase-inhibitor complexes are formed at temperatures below 40° C. Between 40° C. and 55° C., the inhibitor competes with the template DNA for binding to the Taq polymerase, whereas at temperatures above 55° C., the inhibitor is displaced from the polymerase active site. Yet, the inhibitor tends to reduce the obtainable product yield, when primers with lower annealing temperatures are used.

h) Magnesium Sequestration

Since thermostable polymerases are known for a long time to be active only in presence of $Mg^{2+}$ cations, a sequestration of magnesium prior to the start of the thermocycling protocol has been attempted in order to avoid mispriming and unspecifying primer extension. As disclosed in U.S. Pat. No. 6,403, 341, $Mg^{2+}$ may be present in form of a precipitate and thus unavailable at the beginning of the amplification reaction. Upon temperature increase during the first round of thermocycling, the precipitate dissolves and $Mg^{2+}$ becomes fully available within the first 3 cycles. Such a solution has been shown to be fairly applicable and capable of providing good hot start results. On the other hand, such a solution does not allow the preparation of mastermixes containing all reagents except primer and target nucleic acid which are necessary to perform a nucleic acid amplification reaction. As a consequence, inter-assay data reproducibility and data comparisons are complicated. In addition, it has been disclosed to add $Mg^{2+}$ binding peptides to an amplification solution In order to generaste a desired hot start effect (PCT/EP2007/001585).

In view of the outlined prior art it was an object of the invention to provide an improved alternative composition and method for hot start PCR, which allows for an inhibition of unspecific priming and primer extension not only prior to the amplification process itself but also during the thermocycling process. More precisely, it was an object of the invention to provide an alternative composition and method for hot start PCR, where no extension of non specifically annealed primers can take place.

SUMMARY OF THE INVENTION

In a first aspect, the present invention provides a chemical compound comprising the structure

[X$x$-(CH2)$m$-phosphate-Y$y$]$n$ characterized in that
$3 \leq m \leq 6$,
$30 \leq n \leq 60$
each x and y is independently from each other 0 or 1
each X and Y is independently from each other an entity being selected from a group consisting of nucleoside residues, (deoxy-) nucleoside residues, derivatized nucleoside or (deoxy-) nucleoside residues and nucleoside or (deoxy-) nucleoside analogs,
provided that each m, x, and y are independently selected for each [X$x$-(CH2) m-phosphate-Y$y$] unit and further provided that the terminal X can also be an —OH group or a phosphate group, and further provided that the terminal Y can also be a —H or a (CH$_2$)m-OH group.

In a second aspect, the present invention is directed to a composition comprising
a compound as disclosed above
a DNA polymerase,
and desoxy-oligonucleoside triphosphates In a specific embodiment, said composition further comprises a randomized 5-8 mer oligonucleotide, characterized in that said oligonucleotide comprises a modification with an organic hydrophobic moiety.

In a third aspect, the present invention provides a kit comprising
a compound as disclosed above
a DNA polymerase, and desoxy-oligonucleoside triphosphates In a specific embodiment, the kit further comprise a randomized 5-8 mer oligonucleotide, characterized in that said oligonucleotide comprises a modification with an organic hydrophobic moiety.

In a fourth aspect, the present invention provides a method comprising the steps of
  providing a sample containing nucleic acid
  providing a composition as disclosed above
  providing at least a first oligonucleotide primer,
  performing a polymerase catalyzed primer extension reaction In one embodiment, said nucleic acid is DNA. In another embodiment, said nucleic acid is RNA and wherein said DNA polymerase comprises reverse transcriptase activity.

In a specific embodiment, said polymerase is a thermostable polymerase and the reaction is monitored in real time. Subsequently, a melting curve analysis may be performed.

BRIEF DESCRIPTION OF THE FIGURES

Lanes 1 to 6: Control reaction in the absence of additive with 50 ng, 25 ng, 10 ng, 5 ng, 1 ng, 0 ng template DNA, respectively.

Lanes 7 to 12: PCR reaction in the presence of _X40_ (0.3 mM) with 50 ng, 25 ng, 10 ng, 5 ng, 1 ng, 0 ng template DNA, respectively.

Lanes 13 to 18: PCR reaction in the presence of _X40_ (0.15 mM) with 50 ng, 25 ng, 10 ng, 5 ng, 1 ng, 0 ng template DNA, respectively.

Lanes 19 to 24: PCR reaction in the presence of _X40_ (0.075 mM) with 50 ng, 25 ng, 10 ng, 5 ng, 1 ng, 0 ng template DNA, respectively.

Lanes 25 to 30: PCR reaction in the presence of _X40_ (0.0375 mM) with 50 ng, 25 ng, 10 ng, 5 ng, 1 ng, 0 ng template DNA, respectively.

Lanes 31 to 36: PCR reaction in the presence of _X40_ (0.018 mM) with 50 ng, 25 ng, 10 ng, 5 ng, 1 ng, 0 ng template DNA, respectively.

_a: First strand cDNA synthesis in the presence of _X40_, and subsequent PCR in the absence of _X40_,
_b: First strand cDNA synthesis in the presence of _X40_, and subsequent PCR in the presence of _X40_,
_c: First strand cDNA synthesis in the absence of _X40_, and subsequent PCR in the absence of _X40_,
_d: First strand cDNA synthesis in the absence of _X40_, and subsequent PCR in the presence of _X40_.

DETAILED DESCRIPTION OF THE INVENTION

The present invention provides a new and improved solution for performing a primer extension reaction with increased specificity. In particular, the present invention provides a new and improved solution for performing a nucleic acid amplification reaction with improved specificity. The so called hot start effect results in effective inhibition of undesired primer elongations. Undesired primer elongations result from accidental hybridization events wherein primers are at least partially hybridized to any sequence in a nucleic acid sample which is different from the actual primer binding side of the nucleic acid target.

Compounds According to the Present Invention

The present invention provides a chemical compound comprising the structure characterized in that
$3 \leq m \leq 6$,
$30 \leq n \leq 60$
each x and y is independently from each other 0 or 1,
each X and Y is independently from each other any photometrically measurable entity,
provided that each m, x, and y is independently selected for each [Xx-Cm-phosphate-Yy] unit and further provided that the terminal X can also be an —OH group or a phosphate group, and further provided that the terminal Y can also be a —H or a Cm —OH group.

The inventive compound has been designed to act as a reversible binding partner for $Mg^{2+}$ ions at low temperatures. In contrast, the compound does not seem to have a reasonable affinity for binding to DNA polymerases. Respective experiments in order to determine binding rates of Taq polymerase towards several immobilized compounds with a structure according to the present invention in a BIAcore 2000 instrument failed to reveal of any detectable specific binding affinity.

Upon temperature increase the $Mg^{2+}$ ions are released into the solution again. It is well known for polymerase catalyzed primer extension reactions that the concentration of $Mg^{2+}$ ions plays a crucial role for the specificity and processivity of the reactions. Thus, if at the beginning of a polymerase chain reaction, $Mg^{2+}$ ions are reversibly removed from the solution by a temperature dependent non covalent binding to the inventive compound which is present in the sample, a desired hot start effect is generated: Undesired polymerase activity at low temperature which is based on extension of primers which are unspecifically bound to false target regions of the nucleic acid sample is inhibited. Upon reversible release of $Mg^{2+}$ ions from the inventive compound, the effective concentration of $Mg^{2+}$ ions is increased again and specific primer extension by the polymerase can take place.

Moreover due to the fact that the binding between the inventive compound and the $Mg^{2+}$ is reversible in a temperature dependent manner, the desired hot start effect is not only achieved prior to the first temperature increase at the start of the polymerase chain reaction, but also occurs during each annealing phase at subsequent cycles during the complete amplification protocol.

For each unit "[Xx-(CH2)m-phosphate-Yy]", X and Y may either be absent or represent a photometrically measurable entity. Due to ease of synthesis reasons, however, most or all units of an inventive compound are preferably identical. Furthermore, if all units are identical, it is advantageous, if either only X or only Y is present within each unit.

According to the present invention, the inventive compound is preferably composed of 30 to 60 of said units. While at least 30 units are required in order to generate the desired hot start effect, the upper limit of 60 units is renders the inventive compound easy to synthesize by methods as will be disclosed below.

The inventive compound carries a photometrically measurable entity in order to facilitate concentration adjustment via

UV or visible spectroscopy. Therefore, in principle, any moiety which is stable towards the conditions of standard olgionucleotide syntheisis and with an absorption greater than 250 nm is suitable.

Preferably such photometrically measurable entities for example are (deoxy-) nucleoside residues such as deoxy-Adenosine, desoxy-Guanosine, desoxy-Cytosine, desoxy-Thymidine, or desoxy-Uridine or derivatized nucleotide residues or nucleotide analogs, the presence of which is detectable be respective UV absorption measurement at 260 nm.

Other examples for photometrically measurable entities may be selected from a group consisting of aromates like dinitrophenyl or phenyl, polyaromates like pyrene or heteroaromates like acridin and fluorescent and non flourescent dyes. Like for example Fluoresceines, Rhodamines, Oxazines, Cyanines or Azo dyes.

Thus, in the context of the present invention, X or Y independently from each other may either be absent or a dye or an optionally derivatized nucleoside. In those cases where either X or Y represent internal entities of the compound, said X and Y moieties preferably are (deoxy-) nucleoside residues such as desoxy-Adenosine, desoxy-Guanosine, desoxy-Cytosine, desoxy-Thymidine, or desoxy-Uridine.

In one embodiment, the compound comprises the structure

X—[(CH$_2$)$m$-phosphate]$n$-Y characterized in that
$3 \leq m \leq 6$,
$30 \leq n \leq 60$
X is either a hydroxy or a phosphate group, and
Y is either a hydroxy group or a photometrically measurable entity such as an optionally derivatized (deoxy-) nucleoside residue.
Preferably, all units [(CH$_2$)$m$-phosphate] are identical.
In another embodiment, the compound comprises the structure X—[CH$_2$)$m$-phosphate-Y]$n$ characterized in that
$3<m<6$,
$30<n<60$
X is either a hydroxy or a phosphate group, and
each Y is either hydroxy or a photometrically measurable entity such as an optionally derivatized (deoxy-) nucleoside residue.
Preferably, all units —[(CH$_2$)m-phosphate-Y] are identical.
In a further embodiment, the compound comprises the structure

[X—(CH$_2$)$m$-phosphate]-Y$n$ characterized in that
$3 \leq m \leq 6$,
$30 \leq n \leq 60$
each X is a photometrically measurable entity such as an optionally derivatized (deoxy-) nucleoside residue, and Y is a hydroxy group.
Preferably, all units —[X—(CH$_2$)m-phosphate] are identical.
The spacing between the phosphate groups of the different units depends on the number of C atoms in conjunction with the presence or absence of internal X and Y moieties. According to the present invention, the spacing is chosen in such a way that it effectively allows for a kind of complex bonding, i.e. a non covalent interaction between one $Mg^{2+}$ ion and two adjacent phosphate moieties that are present within the inventive compound.

The inventive compound is a polyanion which is predominantly characterized by the central unit (CH$_2$)m-phosphate, wherein m is a natural number between 3 and 6, i.e. the central unit comprises between 3 and 6 C atoms defining the lower limit of minimal spacing between two adjacent phosphate moieties.

Yet, it has also been proven to be possible to insert further X and Y moieties, which extend the length of the chain of atoms connecting the phosphate moieties thereby at the first glance extending the distance between said moieties. However, as will be shown in the example, the presence of X and Y moieties has no negative effect on complex binding of the $Mg^{2+}$ ions. This is most probably due to the sterical flexibility of the inventive compound.

The inventive compounds may be synthesized using standard phosphoramidite chemistry as it is used in the art for chemical synthesis of oligonucleotides. More precisiely, incorporation of [(CH$_2$)m-phosphate] units is achieved by means of using commercially available C-atom linker phosphoramidites which comprise a protected terminal hydroxyl moiety. Incorporation of nucleoside residues as photometrically measurable entities is achieved by means of using commercially available standard nucleoside phosphoramidites. As a starting material, conventional ommercially available Control Pored Glass Particles are used. The inventive compounds can then be cleaved off according to standard methods, resulting in a terminal phosphate or OH or in a terminal nucleosidic moiety.

Compositions According to the Present Invention

In a second aspect, the present invention is directed to a composition comprising
a compound as disclosed above
a DNA polymerase,
and desoxy-oligonucleoside triphosphates Such a composition is particularly useful for the performance of a PCR amplification reaction, because formation of artificial amplification products such as primer dimers is avoided.

The concentration of the inventive compound is chosen in such a way that the specificity and yield of the PCR amplification reaction are optimized. Preferably, the final concentration of the inventive compound is below 0.1 mM in order to avoid any inhibition of amplification of the specific target nucleic acid. Also preferably, the final concentration of the inventive compound is above 0.01 mM in order to achieve a substantial hot start effect.

The DNA polymerase in general may be any enzyme which is capable of performing a template dependent primer extension reaction. Such a template dependent primer extension reaction can occur on all partially double stranded nucleic acid hybrids characterized in that a primer nucleic acid with a free 3' hydroxyl group is hybridized to a template nucleic acid with a single stranded 5' overhang. The template dependent polymerase then catalyzes extension of the 3' end of the primer by means of incorporating nucleotide residues which are always complementary to the nucleotide at the opposite position within the template strand. The reaction uses dNTPs as substrates and results in a release of pyrophosphate.

In one embodiment, said DNA polymerase is an RNA template dependent polymerase or any modification thereof. Such enzymes are usually called reverse transcriptase. Examples are AMV reverse transcriptase or MMLV reverse transcriptase. In particular, Transcriptor Reverse Transcriptase (Roche Applied Science cat. No: 03 531 317 001) is an applicable enzyme in the context of the present invention. Inventive compositions comprising such RNA dependent DNA polymerase are especially useful for all kinds and applications of preparative and analytical cDNA syntheses, and in particular 2-step RT-PCR.

In another embodiment the DNA polymerase is a DNA template dependent DNA polymerase or any mutant or modification thereof. One prominent example is Klenow polymerase (Roche Applied Science Cat. No. 11 008 404 001). Preferably, the DNA polymerase is a thermostable DNA polymerase or any mutant or modification thereof. A typical example is Taq DNA polymerase from *Thermus aquaticus* (Roche Applied Science Cat. No: 11 647 679 001). The DNA dependent DNA polymerase enzymes may or may not have a 3'-5' proofreading activity such as Pwo Polymerase (Roche Applied Science Cat. No: 11 644 947 001). Furthermore the DNA polymerase component of the present invention may be a mix of enzymes with and without proofreading activity such as the Expand High Fidelity system (Roche Applied Science Cat. No: 11 732 641 001). Inventive compositions comprising any kind of thermostable polymerase are specifically useful for performing various preparative or analytical embodiments of the polymerase chain reaction (PCR).

In a further embodiment the DNA polymerase component of the present invention is a thermostable DNA dependent DNA polymerase with additional RNA template dependent reverse transcriptase activity like the polymerase from *Thermus thermophilus* (Roche Applied Science Cat. No: 11 480 014 001) or a mix of a an RNA dependent DNA polymerase (i.e. a reverse transcriptase) and a thermostable DNA dependent DNA polymerase. Inventive compositions comprising such components are particularly useful for analytical performance of one-step RT-PCR.

The deoxynucleotide triphosphates (dNTPs) are usually a mixture of dATP, dCTP, dGTP and dTTP, however, in some specific instances, only 3 or less different kinds of dNTP may be used. Moreover, such a dNTP may be chemically modified in any way, as long as said building block is still capable of being incorporated into the nascent polynucleotide chain by the polymerase. For example, said modified nucleotide compounds may carry a Biotin or a fluorescent compound modification at the respective base moiety. Furthermore, at least one member of the dNTP mixture can be partially or fully substituted by a dNTP analog like 7 deazadGTP.

The at least one primer oligonucleotide is usually a desoxy-oligonucleotide which is completely or almost completely complementary to a specific region of the target nucleic acid. Furthermore, said primer moiety must have a free 3' hydroxyl group so that it is extendible by a DNA polymerase. For specific purposes, such a primer may be chemically modified for example internally or at its 5' end. Examples for frequently used modifications are Biotin labels, Digoxygenin labels and fluorescent labels. Furthermore the primer can comprise modified nucleosides or nucleoside analogs, which are known to improve PCR results e.g. in allelspecific amplifications eg 4' modified bases or universal bases like inosin in order to amplify different alleles that may be present in the same sample.

If a thermostable DNA dependent DNA polymerase is designed for a PCR reaction, a composition according to the present invention comprises usually two primer oligonucleotides hybridizing in opposite orientations to the opposite strands of the target nucleic acid adjacent to the target sequence that shall become amplified. It is also possible that a composition of the present invention comprises multiple pairs of oligonucleotide PCR primers for multiplex PCR amplification.

In a specific embodiment, said composition further comprises a randomized 5-8 mer oligonucleotide, characterized in that said oligonucleotide comprises a modification with an organic hydrophobic moiety. More exactly, the term "randomized oligonucleotide" refers to a pool of oligonucleotides, the sequences of which represent more or less equally all possible combinations of the 4 different nucleotide residues. Although the addition of 5 mers as well as the addition of 8 mers have been proven to have the desired hot start effect, it has turned out to be particular advantageous, if randomized hexamer oligonucleotides are being used. Said randomized oligonucleotides may be added to the primer extension reaction or the PCR reaction in a concentration range between 10 μM and 1 mM, preferably between 25 μM and 400 μM and most preferably in a concentration of about 100 μM. It has also been proven to be particular advantageous, if the randomized oligonucleotides have a non extendible 3' terminus, which for example may be blocked by a phosphate moiety. This avoids an undesired elongation by the polymerase in case of an accidental hybridization of any of the oligonucleotides at any region of the sample nucleic acid.

The randomized oligonucleotides are chemically modified with an organic hydrophobic moiety. Said moieties usually do not interfere with any type of primer extension reaction. For example, such an organic hydrophobic moiety may be selected from a group of moieties consisting of polycondensed aromatic and heteroaromatic rings like naphthalin, anthracen, phenantren, pyrene, anthraquinones, carbazol phenantrolines, quinolines, etc. or from stilbens, or from steroids like cholesterol. Such hydrophobic moieties may be substituted by non bulky substituents like cyano, methoxy, methyl, nitro and halogens, and are partially known to act as a so called "cap" for stabilizing terminal base pairs. Narayanan, S., et al., Nucleic Acids Research 32(9) (2004) 2901-2911; Dogan, Z., et al., Journal of the American Chemical Society 126(15) (2004) 4762-4763.

Most preferably, such an organic hydrophobic moiety is either a an optionally substituted Pyrene or a an optionally substituted Stilben, which have the following chemical structures:

Most preferably such a pyrene or stilbene is attached to the 5' end of a randomized oligonucleotide whereas the 5' end of such an oligonucleotide has the following structure The organic hydrophobic moiety can be positioned at any part of the randomized oligonucleotide. Preferably however, said modification is introduced at the 5' end of the randomized oligonucleotide. The reason is that such 5' modification can be introduced into the oligonucleotide using phosphoramidite chemistry with an appropriate terminal phosphoramidite according to standard methods that are well known in the art and that pyrene and stilbene phosphoramidites are commercially available.

The randomized oligonucleotide could comprise nucleobase analogs with modified bases like 7 deaza analogs like 7 deaza dG, 7 deaza 8 aza analogs like 7 bromo 7 deaza 8 aza 2 amino dA, or substituted bases like propinyl U, propinyl C, or analogs with modified sugars like 2' methoxy ribose or locked sugars like in LNA, or with ribose analogs like hexitol and altritol. Instead of randomization universal bases like nitroindol or N8 ribosylated-7 deaza 8 aza dA are used whereas preferably only at one position of the randomer is used a universal base instead of randomers. The internucleosidic phosphate could be substituted by an phosphate mimetikum like phosphorthioate or methyl phosphonate or phosphoramidates. The randomized oligonucleotide has preferably one hydrophobic moiety but can be additionally substituted by other hydrophobic moieties, whereas the hydrophobic moieties are independently selected from each other.

Summarizing, compositions comprising inventive polyanion compounds as disclosed above in conjunction with a DNA dependent thermostable DNA polymerase and at least one pair of amplification primers are particularly useful for the performance of a PCR amplification reaction. The reason is that the presence of said polyanions efficiently inhibits polymerase catalyzed formation of artificial amplification products such as primer dimers at temperatures below the annealing temperatures of the respective amplification primers, thereby creating a hot start effect.

It is also within the scope of the present invention, if any of the compositions as defined above further comprises a target nucleic acid sample. The sample usually may for example contain genomic DNA or fragmented genomic DNA in conjunction with DNA dependent DNA polymerases or total cellular or poly-A+ RNA in conjunction with RNA dependent DNA polymerases.

Kits According to the Present Invention

In one particular aspect, the present invention also provides kits for preparing compositions as disclosed in detail above. Thus, the present invention is also directed to a kit comprising at least a DNA polymerase and a compound comprising the structure

[X$x$-(CH$_2$)$m$-phosphate-Y$y$]$n$ characterized in that
$3 \leq m \leq 6$,
$30 \leq n \leq 60$
each x and y is independently from each other 0 or 1
each X and Y is independently from each other any photometrically measurable entity,
provided that each m, x, and y is independently selected for each [X$x$-(CH$_2$)m-phosphate-Y$y$] unit and further provided that the terminal X can also be an —OH group or a phosphate group, and further provided that the terminal Y can also be a —H or a (CH$_2$)m —OH group.

Preferably the photometrically measurable entities for example are (deoxy-) nucleoside residues such as deoxy-Adenosine, desoxy-Guanosine, desoxy-Cytosine, desoxy-Thymidine, or desoxy-Uridine or derivatized nucleoside residues or nucleoside analogs, the presence of which is detectable be respective UV absorption measurement at 260 nm. Thus, in the context of the present invention, X or Y independently from each other may either be absent or an optionally derivatized nucleoside. In those cases where either X or Y represent internal entities of the compound, said X and Y moieties are preferably are (deoxy-) nucleoside residues such as desoxy-Adenosine, desoxy-Guanosine, desoxy-Cytosine, desoxy-Thymidine, or desoxy-Uridine.

In addition, the kit may comprise further components such as Desoxynucleotide Triphosphates (dNTPs) and appropriate buffers as well as other reagent additives, which are useful for performing respective primer extension reactions. Furthermore, parameter specific kits may comprise at least one target specific primer oligonucleotide.

Further in addition, the kit may comprise a randomized 5-8, mer oligonucleotide, characterized in that said oligonucleotide comprises a modification with an organic hydrophobic moiety as disclosed above. In particular, said hydrophobic oiety may be Pyrene.

In a first specific embodiment, the kit is designed for cDNA synthesis and comprises a reverse transcriptase as disclosed above. As a primer component, the kit may comprise either a parameter specific primer for amplification of specific cDNAs.

In a second specific embodiment, the kit is designed for performing PCR and comprises a DNA dependent thermostable polymerase or a mix of DNA dependent thermostable polymerases. The kit may then additionally comprise for example dNTPs and/or a buffer solution and/or at least one or multiple pairs of amplification primers. More specifically, if the kit is designed for one-step RT-PCR, the enzyme component may be a DNA dependent thermostable DNA polymerase which in addition comprises reverse transcriptase activity.

In a third specific embodiment, the kit is designed for 2-step RT-PCR and may comprise various combinations of components selected from the components of the first and second embodiment as disclosed above.

In addition, kits according to the second and third specific embodiments may comprise components which are useful for the detection of PCR amplification products. For example, if the kit is designed for Real Time PCR (=qPCR), such a kit may additionally comprise a double stranded DNA binding dye component such as SybrGrecn (Roche Applied Science Cat. No: 04 707 516 001) or the LC480 ResoLight dye (Roche Applied Science Cat. No: 04 909 640 001). Alternatively, such a kit may additionally comprise fluorescently labeled hybridization probes such as TaqMan probes (U.S. Pat. No. 5,804,375), Molecular Beacons (U.S. Pat. No. 5,118,801), FRET hybridization probes (U.S. Pat. No. 6,174,670), or Simple Probes (WO 02/14555).

Methods According to the Present Invention

The present invention is not only directed to compositions and kits but also to methods of performing primer extension reactions in general and PCR or reverse transcription reactions in particular. Thus, in its broadest sense, a method according to the present invention comprises the steps of
providing a sample suspected to contain said target nucleic acid
adding any of the compositions as disclosed above, and performing at least a first primer extension reaction.

More precisely, a method according to the present invention comprises the steps of
providing a sample suspected to contain said target nucleic acid
adding
a DNA polymerase
Deoxynucleotides
at least one primer oligonucleotide, and a chemical compound comprising the structure characterized in that
$3 \leq m \leq 6$,
$30 \leq n \leq 60$
each x and y is independently from each other 0 or 1,
each X and Y is independently from each other any photometrically measurable entity,
provided that each m, x, and y is independently selected for each [Xx-(CH$_2$)m-phosphate-Yy] unit and further provided that the terminal X can also be an —OH group or a phosphate group, and further provided that the terminal Y can also be a —H or a (CH$_2$)m —OH group,
performing at least a first primer extension reaction.

Preferably the photometrically measurable entities for example are (deoxy-) nucleoside residues such as deoxy-Adenosine, desoxy-Guanosine, desoxy-Cytosine, desoxy-Thymidine, or desoxy-Uridine or derivatized nucleoside residues or nucleoside analogs, the presence of which is detectable be respective UV absorption measurement at 260 nm. Thus, in the context of the present invention, X or Y independently from each other may either be absent or an optionally derivatized nucleoside. In those cases where either X or Y represent internal entities of the compound, said X and Y moieties are preferably are (deoxy-) nucleoside residues such as desoxy-Adenosine, desoxy-Guanosine, desoxy-Cytosine, desoxy-Thymidine, or desoxy-Uridine.

The concentration of the chemical compound is chosen in such a way that the specificity and yield of the PCR amplification reaction are optimized. Preferably, the final concentration of the inventive compound is below 0.1 mM in order to avoid any inhibition of amplification of the specific target nucleic acid. Also preferably, the final concentration of the inventive compound is above 0.01 mM in order to achieve a substantial hot start effect.

In a first embodiment, the sample is either total or poly-A+ RNA, the DNA polymerase is a reverse transcriptase and the primer oligonucleotide is a specific primer that is complementary to a specific type of cDNA.

In a second embodiment, the sample is derived from genomic DNA, the DNA polymerase is a thermostable DNA polymerase or a mixture of thermostable DNA polymerases and at least one pair or multiple pairs of amplification primers are added prior to a PCR amplification reaction. Preferably, said nucleic acid amplification reaction is a polymerase chain reaction which is monitored in real time according to standard methods known in the art (see, for example U.S. Pat. Nos. 5,210,015, 5,338,848, 5,487,972, WO 97/46707, WO 97/46712, WO 97/46714).

In a particular embodiment, the amplification product generated is subjected to a melting curve analysis (U.S. Pat. Nos. 6,174,670, 6,569,627) by means of subjecting the amplification product to a thermal gradient over time. In this type of experiment, fluorescence intensity is monitored, which is due either to the binding of a respectively labeled hybridization probe, or due to the fluorescence originating from a DNA binding dye. Then, the first derivative of the decrease in fluorescence intensity due to the melting of the hybridization probe or the two strands of amplicon, respectively, is plotted against the temperature gradient.

Summarizing, it can be stated the inventive method comprises several advantages over methods already disclosed in the art. The presence of a compound according to the present invention during a primer extension reaction such as a reverse transcription or a PCR or an RT-PCR clearly results in an increase in the specificity of the respective reaction.

One major advantage of the inventive method is the ease of use and the short activation time to eliminate the inhibition of the polymerase at low temperatures. Simply, a chemical compound comprising the structure [Xx-(CH$_2$)m-phosphate-Yy]n, characterized in that $3 \leq m \leq 6$, $30 \leq n \leq 60$, each x and y is independently from each other 0 or 1, and each X and Y is independently from each other any photometrically measurable entity, provided that the terminal X can also be an —OH group or a phosphate group, and further provided that the terminal Y can also be an —OH group needs to be added to a PCR reaction set up. Optionally, randomized 5-8 mer oligonucleotide, characterized in that said oligonucleotide comprises a modification with an organic hydrophobic moiety can be added in order to further optimize the desired hot start effect.

During PCR thermocycling the denaturation time prior to each cycle which is usually required to separate double stranded DNA templates into single strands is sufficient to dissociate the Mg$^{2+}$ ions from the inventive compound. Thus, unspecific primer elongation is not only inhibited prior to the start of the PCR reaction, but throughout the complete thermocycling process.

Furthermore, said inventive compounds can be synthesized according to standard phosphoramidate chemistry methods which are well established in the art. Linker phosphoramidites as well as nucleoside residues can be introduced during synthesis of the inventive compound with unlimited flexibility. Thus the production costs for the inventive PCR additive are fairly low as compared to other hot start solutions.

In addition, the inventive methods, compositions and kits can be generically used for any kind of primer extension, reverse transcription or PCR amplification, irrespective of what specific target nucleic acid sequence shall be prepared, amplified, detected, or analyzed.

Specific Embodiments

EXAMPLE 1

Synthesis of 3 Compounds According to the Present Invention

_X40_ compound: a compound comprising 8 [C$_3$-phosphate]$_5$ units, each unit interrupted by a thymidin nucleoside, with additional thymidine residues at both ends.

_X30_ compound: a compound comprising 6 [C$_3$-phosphate]$_5$ units, each unit interrupted by a thymidin nucleoside, with additional thymidine residues at both ends.

_X20_ compound: a compound comprising 4 [C$_3$-phosphate]$_5$ units, each unit interrupted by a thymidin nucleoside, with additional thymidine residues at both ends (not covered by the scope ogf the claimed invention).

Synthesis was carried out similar to an oligonucleotide synthesis on a 4 times 10 μmol scale on an ABI 394 synthesizer. All other chemicals for the standard synthesis were obtained from Glen Research. Commercially available dT CPG was used as the support material dT phosphoramidite (5'-Dimethoxytrityl-2'-deoxyThymidine,3'-[(2-cyanoethyl)-(N,N-diisopropyl)]-phosphoramidite) and Spacer phosphoramidite C3 (3-(4,4'-Dimethoxytrityloxy)propyl-1-[(2-cyanoethyl)-(N,N-diisopropyl)]-phosphoramidite) was used for solid phase synthesis The standard oligonucleotidede synthesis protocol was used for the synthesis. The product was cleaved from the support for 2 h at room temperature with a conc ammonia in water. The crude oligo was purified by IEX chromatography on a MonoQ column. Chromatography: buffer A: 10 mM NaOH in water, buffer B: 10 mM NaOH 1 M NaCl in water. The UV absorption of the eluant was measured at 260 nm. A main fraction was obtained which contained the desired full length product. The salt was removed by dialysis and the solvent was removed by using a rotary evaporater. The concentration was adjusted by measuring the absorption at 260 nm. (extinction coefficient was calculated by standard program)

EXAMPLE 2

PCR in the Presence of Various Concentrations of X40

Figure 1:
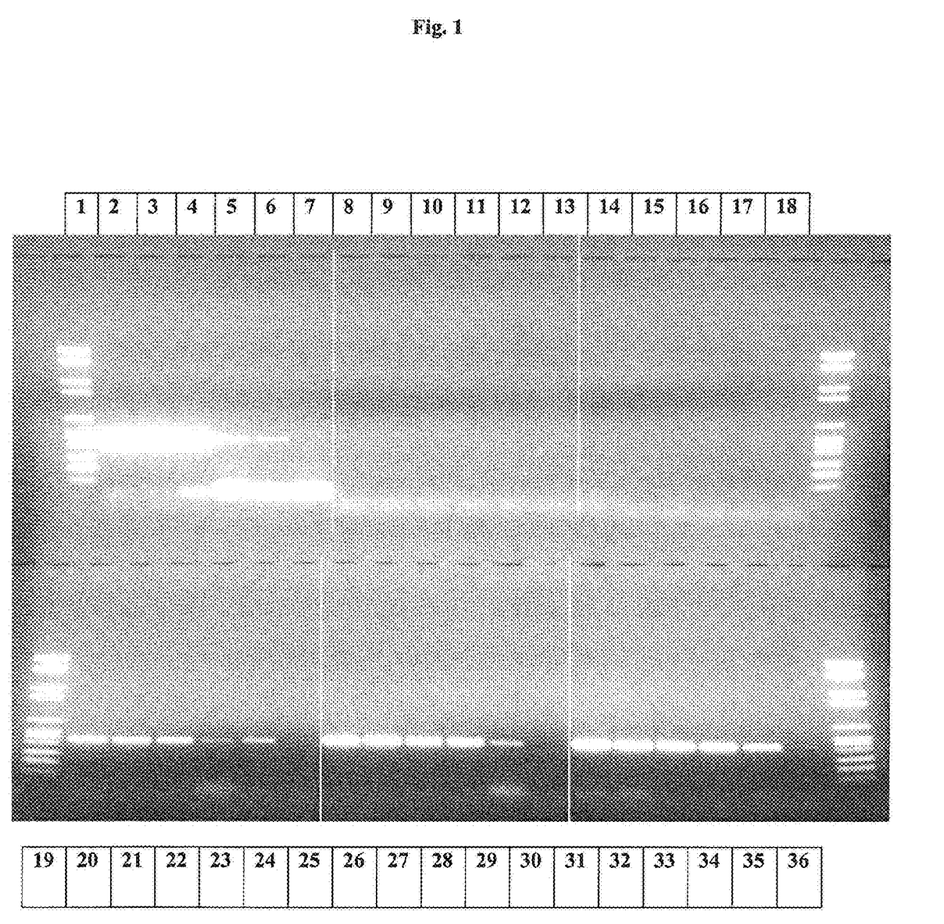
FIG. 1: PCR amplification of various amounts of target DNA in the presence of various amounts of compound X40 (Example 2)
Figure 2A:
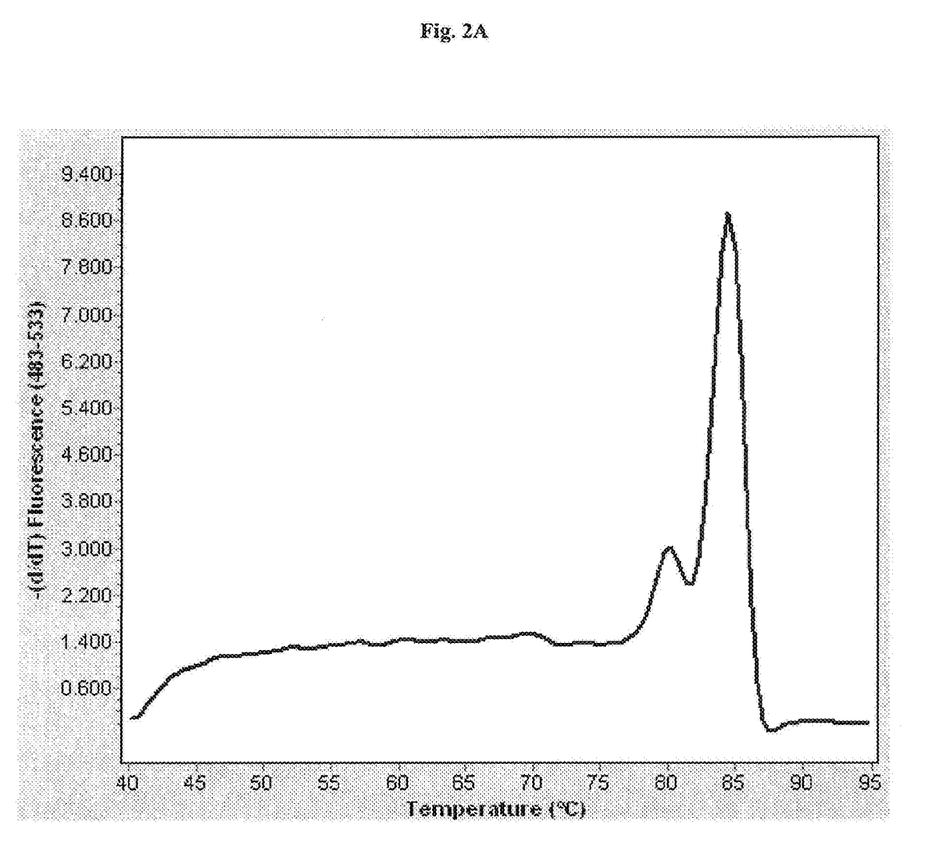
FIG. 2: Melting curve analysis subsequent to RT-PCR (Example 5)
Figure 2B:
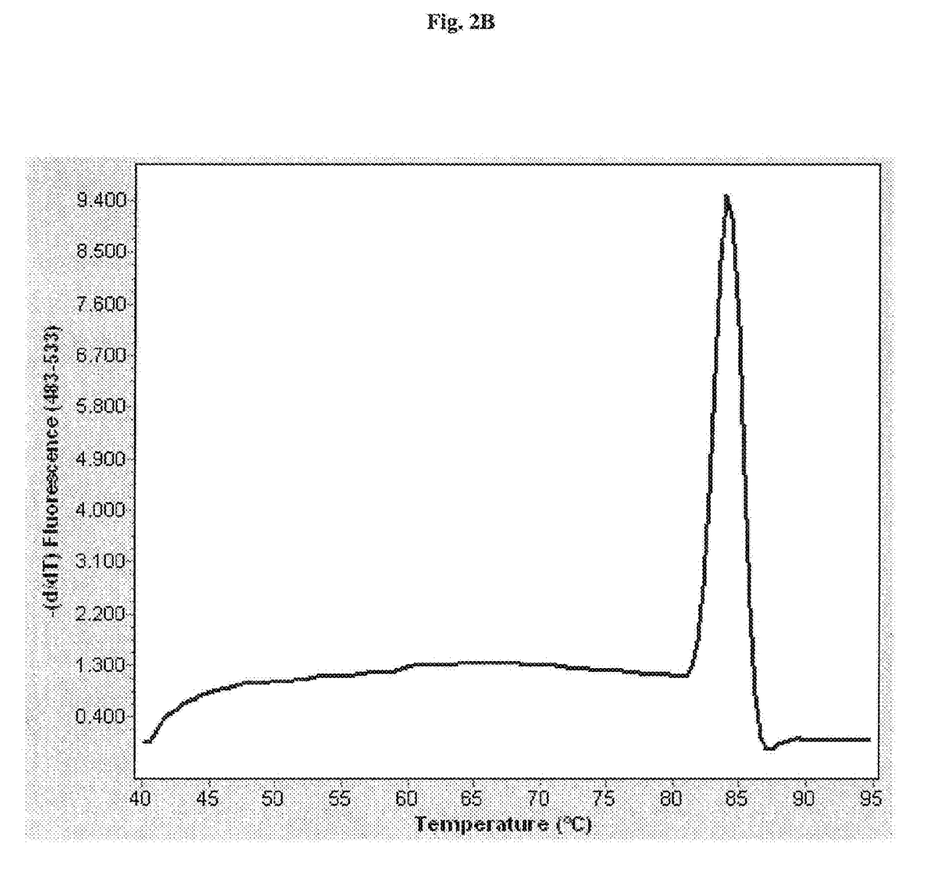
Figure 2C:
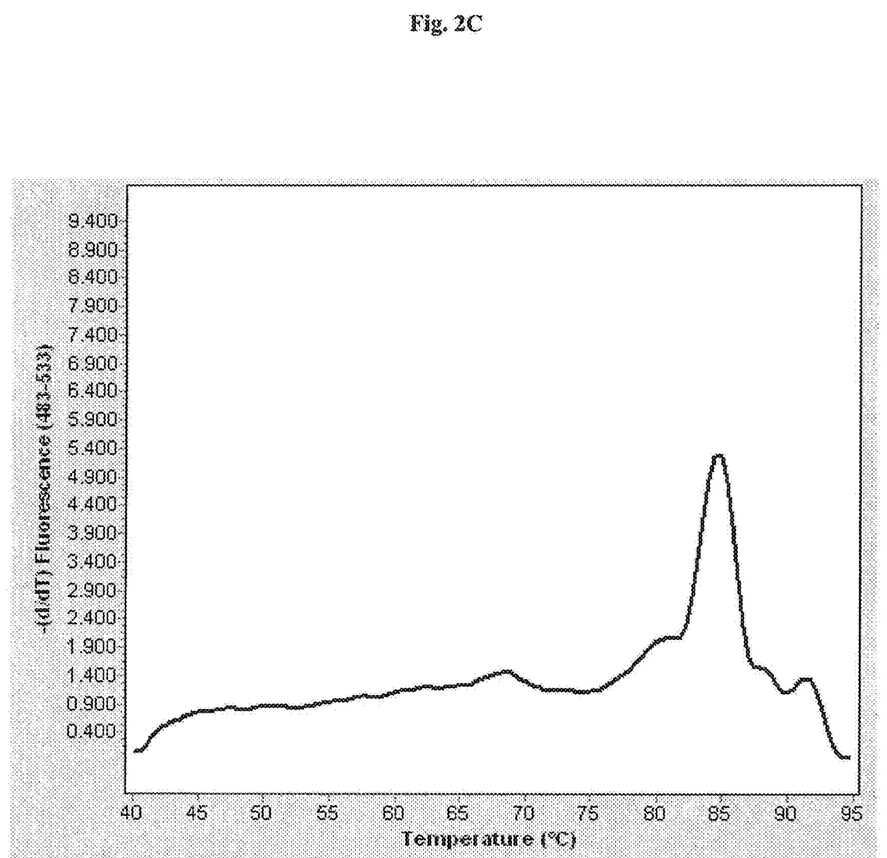
Figure 2D:
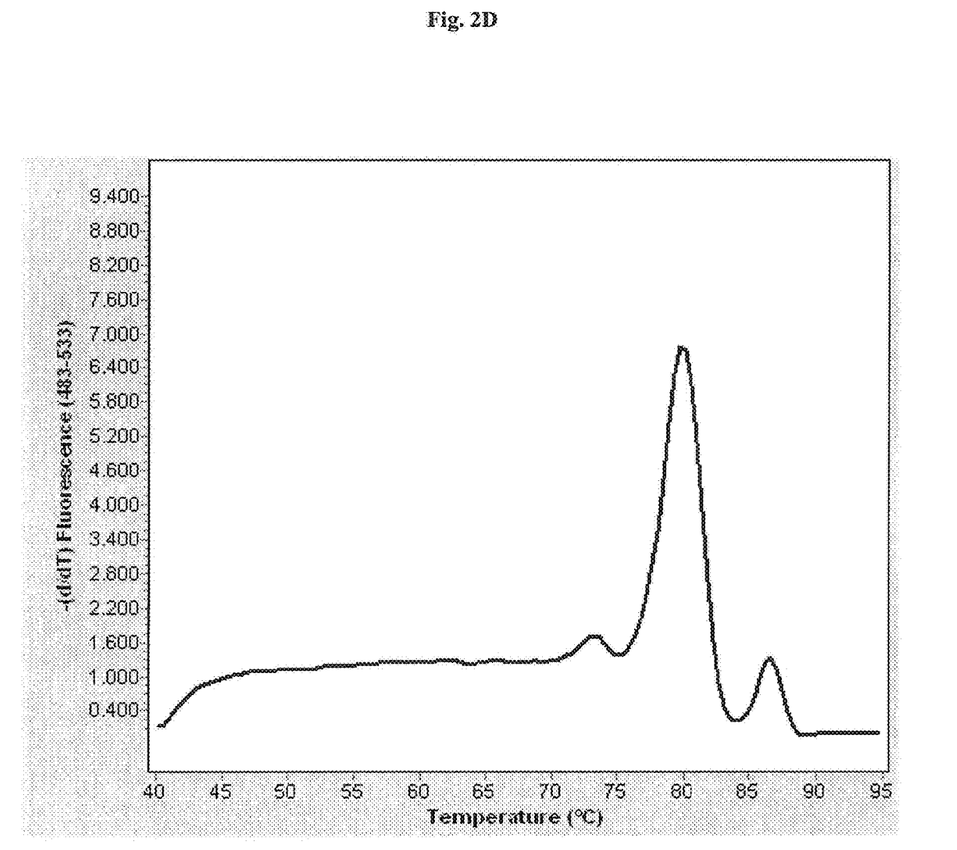

Various concentrations of _X40_ were analyzed in PCR. PCR reactions in the presence or absence of _X40_ were performed in 50 μl volume containing 50 ng, 25 ng, 10 ng, 5 ng or 1 ng of human genomic DNA, 30 mM Tris-HCl, pH 8.6, 50 mM KCl, 1.5 mM MgCl$_2$, 0.4 μM primer (SEQ. ID. No: 1: CTG AGA ATC GGC AAG AGA CC and SEQ. ID. No: 2 CTG CAC AGT AAT GCA TGC CG), 0.2 mM deoxynucleotides, and 2.5 units Taq DNA polymerase. DNA was amplified with the following cycle conditions: Initial denaturation for 4 minutes at 94° C. and 35 cycles with 20 seconds denaturation at 94° C., 30 seconds annealing at 62° C. and 60 seconds elongation at 72° C. The amplification products were separated on agarose gel and visualized by ethidium bromide staining. Results are shown in FIG. 1.

The control reaction in the absence of additives showed the increasing formation of primer dimer with decreasing target concentrations. In the presence of high concentrations above 0.1 mM _X40_, the DNA synthesis was inhibited. With concentrations below 0.1 mM or lower concentrations of _X40_, primer dimer formation was strongly reduced.

EXAMPLE 3

Real Time PCR in the Presence of X40, X30, and X20

_X40_, _X30_ and _X20_ were analyzed in real time PCR. PCR reactions were performed in the presence of _X40_(40 μM or 70 μM final concentration), _X30 _(70 μM or 100 μM final concentration), _X20_ (various concentrations between 40 and 100 μM) or in the absence of additives. The reactions contained 30 ng, 3 ng or 0.3 ng of human genomic DNA, 50 mM Tris-HCl, pH 8.6, 0.2 mM CHAPS, 1 mM BigChap, 20 mM KCl, 3 mM MgCl$_2$, 0.5 μM primer each (SEQ. ID. No: 3: GGA AGT ACA GCT CAG AGT TCT and SEQ. ID. No: 4: GAA TCT CCA TTC ATT CTC AAA AGG ACT), 0.2 mM deoxynucleotides, SYBR Green diluted 1:20 000 (Molecular Probes) and 2.4 units of Taq DNA polymerase. PCR was conducted in 20 μl volumes in a LightCycler®480 Instrument (Roche Applied Science Cat No. 05 015 278 001) with the following cycle conditions: Initial denaturation for 2 min at 95° C. and 45 cycles with 1 second denaturation at 95° C., 5 seconds annealing at 65° C. and 15 seconds elongation at 72° C. A melting profile was measured according to the manufacturer's instructions with 1 second at 95° C., 30 seconds at 60° C. and continuous heating up to 95° C. with 5 acquisitions/centigree. Real time PCR detection was performed using the SybrGreen modus.

Melting curve analysis revealed that in the absence of additives, a second product with lower melting temperature was formed. In the presence of _X40_ or _X30_ the formation of the unspecific product was reduced, while the presence of _X20_ (which is not covered by the scope of the present invention) did not result in reduction of unspecific product formation.

EXAMPLE 4

Combination of X40 with Pyren Capped Hexamers as Additives for RT-PCR

The effect of _X40_ was tested in combination with pyrene capped hexamers in a one-step real time RT-PCR with a primer pair which causes a series of unspecific products in addition to the specific product.

The reaction mixture consisted of 0.5 μM primers each (SEQ. ID. No: 5: CCC TCT TCA CCC TGG CTA A and SEQ. ID. No: 6: ACC CTC ITC ACC CTG GCT A), 0.2 μM dATP, 0.2 μM dCTP, 0.2 μM dGTP, 0.6 μM dUTP, 30 mM Tris-HCl, pH 8.5, 30 mM KCl, 3 mM $MgCl_2$, 0.1 mg/ml BSA, 0.01% Tween, SYBR Green 1:20 000, 1.2 U of Taq DNA polymerase and 0.6 units of Transcriptor reverse transcriptase (Roche Applied Science Cat. No. 04 379 012 001). X40 was added in 75 μM concentration. An assay mixture with the combination of additives contained 40 μM X40 and 40 μM pyrene capped hexamer. Total RNA from HeLa cells was used as template with 1 ng, 100 pg, 10 pg and 1 pg, respectively. Water was used as no template control. RT-PCR was carried out in a 20 μl volume in a LightCycler®480 Instrument (Roche Applied Science Cat No. 05 015 278 001) with the following cycle conditions: Reverse transcription for 10 min at 50° C., PCR with an initial denaturation for 5 min at 95° C. and 45 cycles with 10 seconds denaturation at 95° C., 10 seconds annealing at 57° C. and 13 seconds elongation at 72° C. A melting profile was measured with 1 second at 95° C., 10 seconds at 40° C. and continuous heating up to 95° C. with 5 acquisitions/centigree according to the manufacturer's instructions.

In the absence of additives many unspecific PCR amplification products were generated. In the presence of _X40_, the number of products was significantly reduced, whereas with the combination of _X40_ and pyrene capped hexamers only one single specific amplification product was formed.

EXAMPLE 5

Real Time RT-PCR

In order to evaluate whether the increase of specificity can also be observed in cDNA synthesis prior to a PCR amplification step, a two-step RT-PCR experiment was performed in a reaction set up close to the conditions of one-step RT-PCR. Four reactions were performed in parallel:
(a) first strand cDNA synthesis with _X40_, and subsequent PCR in the absence of _X40_,
(b) first strand cDNA synthesis in the presence of _X40_, and subsequent PCR in the presence of _X40_,
(c) first strand cDNA synthesis in the absence of _X40_, and subsequent PCR in the absence of _X40_,
(d) first strand cDNA synthesis in the absence of _X40_, and subsequent PCR in the presence of _X40_.

G6PDH forw (SEQ. ID. NO: 7: GCA AAC AGA GTG AGC CCT TC) and G6PDH rev (SEQ. ID. NO: 8: GGG CAA AGA AGT CCT CCA G) were chosen as a primer pair which causes the formation of unspecific products when low amounts of RNA are present in the RT-PCR reaction. cDNA was synthesized in 20 μl reactions containing 0.5 μM primers, 0.6 units of Transcriptor (Roche Applied Sciences, Cat No.: 03531317001), 30 mM Tris.HCl, pH 8.6; 3 mM $MgCl_2$, 200 μM dATP, 200 μM dGTP, 200 μM dCTP, 600 μM dUTP, 20 mM KCl, 0.2 mM CHAPSO, 1 mM BigChap, 125 ng/ml T4 gene 32 protein, SYBR Green in a final dilution of 1:20 000 and 10 pg of total RNA from HeLa cells. Two samples for cDNA synthesis were prepared, one with 100 μM _X40_, the other without _X40_. The reactions were incubated for 10 min at 50° C., 2 min at 95° C. and chilled on ice. Then, both reactions were splitted and PCR was subsequently performed in 20 μl reaction volumes using 2 μl of the cDNA reaction mixtures, 0.5 μM of the primers, 1.2 units of Taq polymerase in the same buffer as described for the cDNA reaction mixture in the presence or absence of additional _X40_ 100 μM final concentration. The four different reactions were incubated in a LightCycler 480 instrument (Roche Applied Science Cat No. 05 015 278 001) at 95° C. for 2 min and 45 cycles of 95° C./10 seconds, 60° C./10 seconds, 72° C./13 seconds. The melting profiles of the amplification products determined according to the manufacturer's instructions are shown in FIGS. 2a-d. In the reactions where _X40_ was present during cDNA synthesis and subsequent PCR (FIG. 2b), only one melting peak representing one single product was formed with the melting point expected. When cDNA synthesis was performed in the absence of _X40_ during PCR (FIGS. 2c and 2d) several products were generated which have melting temperatures different to that of the specific product. Even the presence of _X40_ only during cDNA synthesis but absence during subsequent amplification (FIG. 2a) yielded a better result than complete absence of _X40_. Thus, this result shows that _X40_ is able to suppress unspecific product formation during PCR DNA amplification as well as during reverse transcription of RNA.

What is claimed is:

1. A chemical compound comprising the structure

[X$x$-(CH$_2$)$m$-phosphate-Y$y$]$n$ wherein $3 \leq m \leq 6$, $30 \leq n \leq 60$, each x and y is independently from each other 0 or 1, each X and Y is independently from each other an entity selected from the group consisting of nucleoside residues, deoxynucleoside residues, derivatized nucleoside or deoxynucleoside residues and nucleoside or deoxynucleoside analogs, provided that each m, x, and y are independently selected for each [Xx-(CH$_2$)m-phosphate-Yy] unit and further provided that the terminal X can also be an OH group or a phosphate group, and further provided that the terminal Y can also be an H or a (CH$_2$)m-OH group.

2. A composition comprising
a compound according to claim 1,
a DNA polymerase, and
desoxyoligonucleotides.

3. A composition according to claim 2 further comprising a randomized 5-8 mer oligonucleotide, wherein said oligonucleotide comprises a modification comprising an organic hydrophobic moiety.

4. A kit comprising
a composition according to claim 2,
a DNA polymerase, and
desoxyoligonucleotides.

5. A kit according to claim 4, further comprising a randomized 5-8 mer oligonucleotide, wherein said oligonucleotide comprises a modification comprising an organic hydrophobic moiety.

6. A method comprising the steps of
providing a sample containing nucleic acid,
providing a composition according to claim 3,
providing at least a first oligonucleotide primer, and
performing a polymerase catalyzed primer extension reaction.

7. A method according to claim 6 wherein said nucleic acid is RNA and wherein said DNA polymerase comprises reverse transcriptase activity.

8. A method according to claim 6 wherein said polymerase is a thermostable polymerase and the reaction is monitored in real time.

9. A method according to claim 8 wherein the amplification product generated by said amplification is subjected to a melting curve analysis.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctgagaatcg gcaagagacc                                               20
```

-continued

```
<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgcacagta atgcatgccg                                                     20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggaagtacag ctcagagttc t                                                   21

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaatctccat tcattctcaa aaggact                                             27

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccctcttcac cctggctaa                                                      19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
accctcttca ccctggcta                                                      19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcaaacagag tgagcccttc                                                     20

<210> SEQ ID NO 8
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggcaaagaa gtcctccag                                              19
```